United States Patent [19]

Monticello

[11] Patent Number: 5,376,387
[45] Date of Patent: Dec. 27, 1994

[54] HYDROGEN PEROXIDE COMPOSITION

[75] Inventor: Michael V. Monticello, Saddle Brook, N.J.

[73] Assignee: Eastman Kodak Company, Rochester, N.Y.

[21] Appl. No.: 93,286

[22] Filed: Jul. 16, 1993

[51] Int. Cl.$^5$ .................. A61K 33/40; A61K 31/41
[52] U.S. Cl. ........................................ 424/616; 514/359
[58] Field of Search ........................ 514/359; 424/616

[56] References Cited

U.S. PATENT DOCUMENTS

| | | | |
|---|---|---|---|
| 4,469,614 | 9/1984 | Martin | 252/106 |
| 4,477,438 | 10/1984 | Willcockson et al. | 424/130 |
| 4,518,585 | 5/1985 | Greene | 424/130 |
| 4,557,898 | 12/1985 | Greene | 422/28 |
| 4,654,374 | 3/1987 | Martin | 514/698 |
| 4,758,367 | 7/1988 | George | 252/75 |
| 5,077,008 | 12/1991 | Kralovic | 422/37 |
| 5,133,890 | 7/1992 | O'Neil | 252/51.5 |

*Primary Examiner*—Zohreh Fay
*Attorney, Agent, or Firm*—J. Jeffrey Hawley

[57] ABSTRACT

Aqueous acidic compositions containing hydrogen peroxide and a methyl substituted benzotriazole derivative have been found to have a high stability and do not promote corrosion when used to clean metal objects.

20 Claims, No Drawings

HYDROGEN PEROXIDE COMPOSITION

FIELD OF THE INVENTION

This invention relates to hydrogen peroxide compositions that may be used to clean surfaces.

BACKGROUND OF THE INVENTION

Hydrogen peroxide is widely known as an excellent hard surface sterilant and disinfectant that is environmentally safe and cost effective. Other sterilant/disinfectant agents such as phenolics and aldehydes are not as environmentally and toxicologically as sound as hydrogen peroxide. For example, although glutaraldehyde compositions are widely used among infection control staff, glutaraldehydes are associated with disadvantages such as skin sensitization, toxicity and chemical waste management.

Despite its superior efficacy for disinfecting and sterilization uses, hydrogen peroxide has not been widely used in medical facilities for cleaning hard metal surfaces because hydrogen peroxide oxidizes metals, such as, copper and brass. Many hospital instruments and scopes contain copper and/or brass components which may become irreversibly damaged by corrosion when exposed to hydrogen peroxide solutions.

Previous attempts to reduce the corrosive affects of hydrogen peroxide solutions have been met with only limited success. For example, when known corrosion inhibitors such as phenyl sulfonic acid, phosphate esters, sodium molybdate, alkanolamines, or benzotriazoles are used, the anti-corrosive activity is either too short-term (because the inhibitor is unstable in the presence of hydrogen peroxide); not observed at all; or the resulting composition leaves an undesirable oxide film residue on hard surfaces upon drying.

In particular, the anti-corrosive agents 1,2,3-benzotriazole and tolyltriazole are known to decrease the corrosive activity of hydrogen peroxide. Both, however, are unstable in the presence of hydrogen peroxide and lose effectiveness after a short storage period. The Comparative Examples hereinafter illustrate the limited stability of 1,2,3-benzotriazole and tolyltriazole in hydrogen peroxide. Hydrogen peroxide compositions with these anti-corrosive agents have a very short shelf life and because the compositions are unstable neither have become accepted compositions useful for cleaning metal surfaces.

Corrosion associated with hydrogen peroxide compositions remains a problem. A stable hydrogen peroxide composition providing a sterilant or disinfectant activity without promoting corrosion to metal surfaces treated with the composition is needed.

SUMMARY OF THE INVENTION

The problem described above has been solved with the discovery of a hydrogen peroxide based aqueous composition comprising:

a) from about 0.25 to about 25 weight % of a methyl substituted triazole derivative of a Formula I as follows:

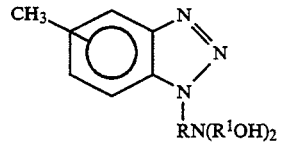

wherein R is a $C_1$–$C_4$ straight or branched alkyl group and $R^1$ is a straight or branched $C_1$–$C_5$ alkyl group;

b) from about 0.5 to about 50 weight % hydrogen peroxide; and c) an acidic buffer wherein said composition has a pH level falling within the range of from about 1 to about 5, and said weight percentages are based on the total weight of the aqueous composition.

Unexpectedly, the methyl substituted triazole derivative does not lose its efficacy as an anticorrosive agent after it is combined with hydrogen peroxide and stored. The inventive composition demonstrates a high level of stability with a good anti-microbial activity. Importantly, the composition does not promote corrosion on metal surfaces, even after the composition is stored for an extended period of time. Thus, the inventive composition unexpectedly exhibits characteristics providing it with a significant commercial advantage over known hydrogen peroxide compositions.

DETAILED DESCRIPTION OF THIS INVENTION

The methyl substituted triazole derivative is as previously defined herein by Formula I (with R and $R^1$ as designated). More preferably, the triazole component is defined wherein R represents a —$CH_2$ group and $R^1$ represents a —$CH_2$, —$CH_2CH_2$, or —$CH_2CH_2CH_2$ group. Most preferably, the triazole component is defined by Formula I wherein R is —$CH_2$ and $R^1$ is —$CH_2CH_2$, as available, for example, as REOMET TM 42, identified as ethanol solution with 75% active ingredient of 2,2'-{[(methyl-1H-benzotriazole-1-yl)methyl-]imino)bis-]obtained from Ciba Geigy, Hawthorne, N.Y.

According to the invention, the methyl substituted triazole derivative is present in an amount sufficient to act as an anti-corrosive agent when stored with hydrogen peroxide for a period of at least about one month at room temperature. When a high concentration level of hydrogen peroxide is present, it is preferred that the concentration level of the methyl substituted triazole derivation also be higher to insure effectiveness as an anti-corrosive agent. Preferably, the triazole derivative is employed in an amount ranging from about 0.1 to about 25 weight %, more preferably from 0.4 to 10 weight %, and most preferably 0.45 to 1 weight %, with said weight % (set forth as 100 % active) based on the total weight of the aqueous composition.

Depending upon the level of antimicrobial activity desired and whether the composition is prepared as a concentrate, the hydrogen peroxide component of the composition may be used in wide range of concentration. A preferred range of concentration of hydrogen peroxide is from about 0.5 to about 50 weight %, more preferably from 1 to 10 weight % and most preferably 7 to 9 weight %, with said weight % (set forth as 100% active) based on the total weight of the aqueous composition.

The composition of the invention preferably has a pH falling within the range of from about 1 to about 5, more preferably below 3, and most preferably falling between 1 and 2. An adjustment of the composition to this pH level may be accomplished by various known techniques. For example, organic and inorganic acid may be used to adjust the pH level, including, hydroxyacetic acid, benzenesulfonic acid, trifluoracetic acid, hydrochloride acid, nitric acid, phosphoric acid, sulfuric acid, sulfamic acid, oxalic acid, and so on. Particularly preferred acids, because of low cost and availability, are sulfamic acid, oxalic acid, phosphoric acid, and mixtures thereof, with phosphoric acid most preferred.

The composition of the invention may optionally have other ingredients present such as aqueous alcoholic tertiary amines, fatty acid alkanolamides, surfactants, or mixtures thereof that are compatible with hydrogen peroxide in acidic aqueous media. Compatibility, as defined herein, indicates the optional component as defined is relatively stable against oxidation and decomposition in the presence of acidic aqueous hydrogen peroxide.

More particularly, suitable surfactants that are compatible with hydrogen peroxide in acidic aqueous media include nonionic, anionic, amphoteric and cationic classes of surfactants and mixtures thereof, as are commercially available and well know in the art. If included, the surfactants are preferably employed in an amount ranging from about 0.01 to about 30 weight %, more preferably from 0.1 to 10 weight %, and most preferably about 0.75 to 1.25 weight %, based on the total weight of the composition.

If employed, examples of suitable nonionic surfactants include, for example, one or more of the following: (1) Ethoxylated fatty alcohols containing from about 11 to about 15 carbon atoms in the alcohol and from about 3 to about 40 moles of ethylene oxide, as commonly available, such as isomeric linear secondary alcohols with 11 to 15 carbon atoms and 9 moles of ethylene oxide and linear primary alcohols with 12 to 15 carbon atoms and 9 moles of ethylene oxide; (2) Block copolymer nonionics such as ethylenediamine reacted copolymers of polyoxyethylene and polyoxypropylene; (3) Ethylene glycol-reacted polyoxyethylene polyoxypropylene copolymers; (4) Alkyl phenol ethoxylates, such as, for example, nonylphenoxypolyethoxyethanol with 9 to 10 moles of ethylene oxide; (5) Alkanolamides, such as, for example, fatty acid alkanolamides having one or two hydroxyethyl or hydroxypropyl groups such as coconut and tallow fatty acid ethanolamide and diethanolamide; and oleic acid diethanolamide; and (6) Amine oxides, and so on. Particularly preferred as nonionic surfactants are the ethylenediamine-reacted copolymers of polyoxyethylene and polyoxypropylene. Examples of suitable anionic surfactants which may be employed include, for example, the following: (1) alkyl sulfate salts, (2) alkyl sulfonate salts, (3) alkali metal alkyl sulfonates, and (4) alkyl aryl sulfonate salts. Examples of suitable amphoteric surfactants which may be employed, include, for example, fatty imidazoline derivatives. Suitable cationic surfactants that may be employed include, for example, ethoxylated amines and quaternary ammonium compounds, and dialkyl quaternary ammonium compounds, and so on, as are well known to those skilled in the art.

The inventive composition may be used to clean a variety of surfaces. The composition is particularly useful for disinfecting and sterilizing surfaces, both animate and inanimate, contaminated with bacterial, fungal and viral microorganisms and/or microbial spores in medical and non-medical situations. The composition offers an excellent alternative to known methods of cleaning surfaces of human and veterinary medicine and surgery and dentistry instruments and objects. Such objects may be treated with the composition at room or elevated temperatures. Also appropriate uses of the composition include industrial and domestic environments because of the excellent disinfecting capabilities of the composition.

The level of antimicrobial activity that is achieved by using the inventive composition is dependent on a number of factors, such as contact time, temperature, and concentration level of the hydrogen peroxide, as known to those skilled in the art. Typically the object to be cleaned, disinfected, and/or sterilized may be contacted with various known techniques, such as immersion, spraying, swabbing, and so on. The highly stable inventive composition is particularly advantageous for immersion techniques because the composition does not promote corrosion. A particularly preferred method for treating objects used in the medical field is by immersion of the object into the inventive composition at room or elevated temperature, preferably from about 20° C. to about 50° C. In this preferred method, the immersion time required to effect sterilization or disinfection is temperature dependent, with progressively less time being required as the temperature is increased. For example, preferred high level disinfectant activity may be achieved at room temperature with a contact time of as little as about 10 minutes. Higher level sporacidal activity may be achieved at room temperature with contact time of as little as about 6 hours or at about 50° C. with contact time of as little as about 10 minutes.

As within the skill of those familiar with the art, the composition may also be prepared as a concentrate which may later be diluted with water prior to usage. An effective amount of the composition for treating surfaces is highly variable, depending upon the level of antimicrobial activity desired and the amount of hydrogen peroxide present in the composition.

Unexpectedly, the composition is stable and may be stored for longer periods than similar compositions of the prior art. For example, the composition maintains stability during storage periods of, for example, from about 1 to about 6 months at 50° C. (or from about 1 to about 2 years or longer when stored at room temperature). The inventive composition thus exhibits an enhanced stability, allowing use of the composition as a cleaner for metal surfaces, such as copper, brass, titanium, zinc, and so on, without causing the corrosion of these metals.

The invention is illustrated by the following examples without, however, being limited thereto.

EXAMPLES

Compositions were submitted to corrosion analysis using metal coupons (discs) that were supplied by Metaspec Co., San Antonio, TX. Copper coupons were composed entirely of copper. Brass coupons were composed of 70% copper and 30% zinc. All coupons were $1 \times 2 \times \frac{1}{8}''$. Visual observation of the corrosion resulted in recording the corrosion on a scale as "none", "slight", "moderate", or "severe".

Compositions A-D were prepared using ingredients in the amounts indicated below. In both Compositions A and B, a methyl substituted triazole derivative REOMET ™ was used as an anti-corrosive agent (as obtained from Ciba Geigy, Hawthorne, NY) as structurally shown as follows:

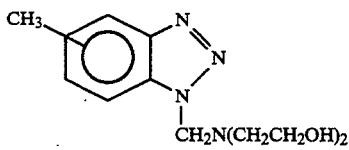

Methyl Substituted Triazole Derivative     MW = 250

In the Comparative Composition C, a 1,2,3-benzotriazole was used as an anti-corrosive agent (COBRATEC ™ 99 obtained from PMC Specialties Group) as structurally shown as follows:

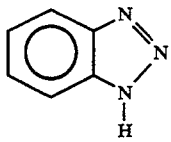

1,2,3-BENZOTRIAZOLE     MW = 119

In the Comparative Composition D, tolyltriazole was used as an anti-corrosive agent (COBRATEC ™ TT-100 obtained from PMC Specialties Group) as structurally represented as follows:

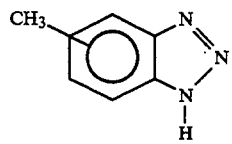

TOLYLTRIAZOLE     MW = 133

The formulations tested as shown below, with weight percentages based on the total weight of the aqueous composition.

INVENTIVE COMPOSITION A

| COMPONENT | WT % |
|---|---|
| Deionized Water | q.s. |
| TETRONIC ™ 908[1.] (100%) | 1 |
| REOMET ™ 42[2.] (75%) | 0.9 |
| Phosphoric Acid[3.] (85%) | 1 |
| Hydrogen Peroxide[4.] (50%) | 15 |
| pH = 1.8 | |

[1.] Alkoxylated diamine nonionic surfactant, BASF Corp., Parsippany, NJ.
[2.] Ethanol solution with 75 weight % of active ingredient of 2,2′-[[(methyl-1H-benzotriazole-1-yl)methyl]imino]bis-, Ciba Geigy, Hawthorne, NY (approximately 0.7 weight % based on 100% active ingredient).
[3.] Monsanto, St. Louis, MO.
[4.] FMC Corp., Princeton, NJ. (7.5 weight % based on 100% active ingredient)

INVENTIVE COMPOSITION B

| COMPONENT | WT % |
|---|---|
| Deionized Water | q.s. |
| TETRONIC ™ 908[1.] (100%) | 1 |
| REOMET ™ 42[2.] (75%) | 0.65 |
| Phosphoric Acid[3.] (85%) | 1 |
| Hydrogen Peroxide[4.] (50%) | 15 |
| pH = 1.8 | |

[1.] Alkoxylated diamine nonionic surfactant, BASF Corp., Parsippany, NJ.
[2.] Ethanol solution with 75 weight % of active ingredient of 2,2′-[[(methyl-1H-benzotriazole-1-yl)methyl]imino]bis-, Ciba Geigy, Hawthorne, NY (approximately 0.5 weight % based on 100% active ingredient).
[3.] Monsanto, St. Louis, MO.
[4.] FMC Corp., Princeton, NJ. (7.5 weight % based on 100% active ingredient)

COMPARATIVE COMPOSITION C

| COMPONENT | WT % |
|---|---|
| Deionized Water | q.s. |
| TETRONIC ™ 908[1.] (100%) | 0.9 |
| COBRATEC ™ 99[2.] (100%) | 0.7 |
| Phosphoric Acid 85%[3.] | 1 |
| Hydrogen Peroxide 50%[4.] | 15 |

[1.] Alkoxylated diamine nonionic surfactant BASF, Parsippany, NJ.
[2.] 1,2,3-benzotriazole, purchased from PMC Specialties Group, Cincinnati, Ohio.
[3.] Monsanto, St. Louis, MO.
[4.] FMC Corp., Princeton, NJ. (7.5 weight % based on 100% active ingredient)

COMPARATIVE COMPOSITION D

| COMPONENT | WT % |
|---|---|
| Deionized Water | q.s. |
| TETRONIC ™ 908[1.] (100%) | 1 |
| COBRATEC ™ TT-100[2.] (100%) | 0.5 |
| ACITROL ™ 5101[3.] | 0.5 |
| Phosphoric Acid 85%[4.] | 1 |
| Hydrogen Peroxide 50%[5.] | 15 |

[1.] Alkoxylated diamine nonionic surfactant, BASF, Parsippany, NJ.
[2.] Tolyltriazole, PMC Specialties/Cincinnati, OH.
[3.] Aqueous isopropyl alcoholic (about 5%) methenamine (about 20%)-fatty acid alkanolamide (about 30%) mixture, E.F. Houghton & Company, Valley Forge, Penn.
[4.] Monsanto, St. Louis, MO.
[5.] FMC Corp., Princeton, NJ. (7.5 weight % based on 100% active ingredient)

Example I

Composition A was stored for 2 months at room temperature. The composition was then tested (without dilution) for antimicrobial activity in the presence of fluid thioglycollate broth and 5% horse serum using the "Use Dilution Method" —Official— as described by the Official Methods of Analysis of the Association of Official Analytical Chemists: 62–63, 11th Ed., Washington, D.C. 1970. The test temperature was at 20° C. Organisms tested were Staphyococcus aureus (ATCC 6538) Pseudomonas aeruginoso (ATCC 15442) and Salmonella choleraesuis (ATCC 10708). Sixty replicates were run for each organism, with the number of carriers +/ten. All replicates tested 0. A double subculture was used for the S. choleraesuis where the results again showed 0 for the 60 replicates.

Example II

Corrosion analysis for Compositions A and B was conducted after each composition had been stored at the elevated temperature of 50° C. for 1 month. Copper and brass coupons were totally immersed in test solutions (not diluted) of Compositions A and B. Visual observation for corrosion was recorded at 24 hours, 48 hours, and 1 week intervals. There was no observation of corrosion ("none") on any of the coupons at the 24 hours, 48 hours, and 1 week time periods for either Composition A or Composition B. Results are summarized in the TABLE.

Example III

The procedure of Example II was repeated for Compositions A and B after the compositions were stored at the elevated temperature of 50° C. for 2 months. There was no observation of corrosion ("none") on any of the coupons tested in Compositions A and B at the 24 hours, 48 hours, and 1 week time periods. Results are summarized in the TABLE.

Example IV

The procedure of Example II was repeated for compositions A and B after the compositions were stored at room temperature for 2 months. There was no observation of corrosion ("none") on any of the coupons tested in Compositions A and B at the 24 hours, 48 hours, and 1 week time periods. Results are summarized in the TABLE.

Comparative Example I

Corrosion analysis for Composition C was conducted after the composition had been stored at 50° C. for 1 month using the method described in Example II with the exception that only copper coupons were tested. Upon visual observation for corrosion, at 24 hours "slight" corrosion was observed, "moderate" corrosion at 48 hours and "severe" corrosion at 1 week. Results are summarized in the TABLE.

Comparative Example II

Composition D was tested for corrosion activity after the composition had been stored at 50° C. for 2 months. The method of testing was as described above in Example II, with the exception that only copper coupons were tested. At 24 hours "severe" corrosion was observed, as shown in the TABLE. Additional observations beyond 24 hours were not made.

TABLE

| CORROSION OF COPPER | | | |
|---|---|---|---|
| | CONTACT TIME | | |
| | 24 hr | 48 hr | 1 week |
| COMPOSITION A, Ex. II (INVENTION at 1 month, 50° C.) | none | none | none |
| COMPOSITION B, Ex. II (INVENTION at 1 month, 50° C.) | none | none | none |
| COMPOSITION A, Ex. III (INVENTION at 2 months, 50° C.) | none | none | none |
| COMPOSITION B, Ex. III (INVENTION at 2 months, 50° C.) | none | none | none |
| COMPOSITION A, Ex. IV (INVENTION at 2 months, room temp.) | none | none | none |
| COMPOSITION B, Ex. IV (INVENTION at 2 months, room temp.) | none | none | none |
| COMPOSITION C, Comp. Ex. I (COMPARISON at 1 month, 50° C.) | slight | moderate | severe |
| COMPOSITION D, Comp. Ex. II (COMPARISON at 2 months, 50° C.) | severe | — | — |

That which is claimed is:
1. An aqueous composition comprising:
a) from about 0.25 to about 25 weight % of a methyl substituted triazole derivative represented by Formula I as follows:

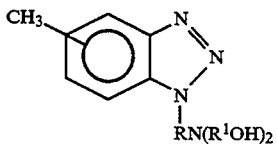

wherein R is a $C_1$-$C_4$ straight or branched alkyl group and $R^1$ is a straight or branched $C_1$-$C_5$ alkyl group;
b) from about 0.5 to about 50 weight % hydrogen peroxide; and
c) an acidic buffer wherein said composition has a pH level falling within the range of about 1 to about 5, and said weight percentages are based on the total weight of the aqueous composition.

2. A composition according to claim 1 wherein said triazole derivative is defined by Formula I wherein R is —$CH_2$ and $R^1$ is —$CH_2CH_2$ and is employed within a concentration range of from about 0.1 to about 25 weight %.

3. A composition according to claim 2 wherein said hydrogen peroxide is employed within a range of from 5 to 10 weight %.

4. A composition according to claim 3 wherein said pH level is below 3 and said triazole derivative is employed within a range of from 0.4 to 10 weight %.

5. A composition according to claim 4 wherein said hydrogen peroxide is employed in an amount ranging from 7 to 9 weight %, said triazole derivative is employed in a concentration range of from 0.45 to 1 weight %, and said pH level falls between 1 and 2.

6. A composition according to claim 1 further comprising a surfactant compatible with hydrogen peroxide.

7. A composition according to claim 6 wherein said surfactant is nonionic and is present in an amount ranging from about 0.01 to 30 weight %.

8. A composition according to claim 7 wherein said surfactant is an ethylenediamine-reacted polyoxyethylene and polyoxypropylene block copolymer.

9. A composition according to claim 8 wherein said surfactant is employed in an amount within the range of 0.75 to 1.25 weight % and said acid buffer is phosphoric acid.

10. A composition according to claim 9 wherein said triazole is defined by Formula I wherein R is —$CH_2$ and $R^1$ is —$CH_2CH_2$ and said triazole is employed in an amount ranging from 0.45 to 1 weight %; said hydrogen peroxide is employed in an amount ranging from 7 to 9 weight %, and said pH level falls between 1 and 2.

11. An aqueous composition consisting essentially of:
a) from about 0.25 to about 25 weight % of a methyl substituted triazole derivative represented by Formula I as follows:

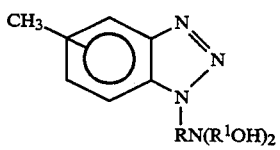

wherein R is a $C_1$-$C_4$ straight or branched alkyl group and $R^1$ is a straight or branched $C_1$-$C_5$ alkyl group;
b) from about 0.5 to about 50 weight % hydrogen peroxide; and
c) an acidic buffer wherein said composition has a pH level falling within the range of about 1 to about 5, and said weight percentages are based on the total weight of the aqueous composition.

12. A composition according to claim 11 wherein said triazole derivative is defined by Formula I wherein R is —$CH_2$ and $R^1$ is —CH2CH2 and is employed within a concentration range of from about 0.1 to about 25 weight %.

13. A composition according to claim 12 further consisting essentially of a nonionic surfactant compatible with hydrogen peroxide wherein said hydrogen peroxide is employed within a range of from 1 to 10 weight %, said triazole is present in an amount ranging from 0.4 to 10 weight %, said acidic buffer is selected from the group consisting of sulfamic acid, oxalic acid, phosphoric acid, and mixtures thereof.

14. A method for disinfecting and sterilizing a surface comprising contacting said surface with an effective amount of an aqueous composition comprising:
a) from about 0.25 to about 25 weight % of a methyl substituted triazole derivative of a Formula I as follows,

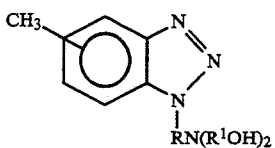

wherein R is a $C_1$–$C_4$ straight or branched alkyl group and $R^1$ is a straight or branched $C_1$–$C_5$ alkyl group;
b) from about 0.5 to about 50 weight % hydrogen peroxide; and
c) an acidic buffer wherein said composition has a pH level falling within the range of about 1 to about 5, and said weight percentages are based on the total weight of the aqueous composition.

15. A method according to claim 14 wherein in said composition said triazole derivative is defined by Formula I wherein R is —$CH_2$ and $R^1$ is —$CH_2CH_2$ and is employed within a concentration range of from about 0.1 to about 25 weight %.

16. A method according to claim 15 wherein in said composition said hydrogen peroxide is employed within a range of from 1 to 10 weight %.

17. A method according to claim 16 wherein said composition further comprises a surfactant compatible with hydrogen peroxide employed in an amount ranging from about 0.01 to 30 weight %.

18. A method according to claim 17 wherein in said composition said surfactant is an ethylenediamine-reacted polyoxyethylene and polyoxypropylene block copolymer.

19. A method according to claim 18 wherein in said composition said triazole is employed within a range of from 0.4 to 10 weight %, said hydrogen peroxide is employed in a range from 1 to 10 weight %.

20. A method according to claim 19 wherein in said composition said triazole is present in amount ranging from 0.45 to 1 weight %, said hydrogen peroxide is present in an amount ranging from 7 to 9 weight %.

* * * * *